United States Patent [19]

Hodosh

[11] Patent Number: 4,654,212
[45] Date of Patent: Mar. 31, 1987

[54] METHOD FOR TREATING HERPES VIRUS

[76] Inventor: Milton Hodosh, 145 Whitmarsh St., Providence, R.I. 02906

[21] Appl. No.: 840,977

[22] Filed: Mar. 13, 1986

Related U.S. Application Data

[63] Continuation of Ser. No. 657,048, Oct. 3, 1984, abandoned, which is a continuation of Ser. No. 467,583, Feb. 18, 1983, abandoned.

[51] Int. Cl.$^4$ .............................................. A61K 33/00
[52] U.S. Cl. ..................................... 424/127; 514/934
[58] Field of Search ......................... 424/127; 514/934

[56] References Cited

U.S. PATENT DOCUMENTS 3,863,006  1/1975  Hodosh .................................. 424/49
4,184,474  1/1980  Van Lenven ....................... 252/106
4,191,750  3/1980  Hodosh ............................. 424/127

Primary Examiner—Leonard Schenkman
Attorney, Agent, or Firm—Salter & Michaelson

[57] ABSTRACT

A method for treating herpes simplex lesions comprising topical application of an agent to the herpetic lesions, said agent comprising a liquid, cream or paste having potassium nitrate as its essential ingredient.

9 Claims, No Drawings

METHOD FOR TREATING HERPES VIRUS

This is a continuation of application Ser. No. 06/657,048 filed Oct. 3, 1984, (abandoned) which is a continuation of application Ser. No. 06/467,583 filed Feb. 18, 1983 (now abandoned).

BACKGROUND AND SUMMARY OF THE INVENTION

There are five herpes viruses that are known to infect humans. They are as follows:

(1) Herpes Simplex Type 1 which causes cold sores, encephalitis and keratitis.

(2) Herpes Simplex Type 2 which causes genital and neonatal herpes.

(3) Varicella-Zoster Virus which causes chicken pox, shingles and herpes zoster.

(4) Epstein-Barr Virus which causes infectious mononucleosis and which may cause certain tumors.

(5) Cytomegalovirus which is responsible for pneumonitis in renal transplant and other immunocompromised patients, congenital malformations including mental retardation and a mononucleosis-like syndrome in young adults and recipients of blood transfusions. Cytomegalovirus infections and their complications are now at near epidemic proportions in the male homosexual population.

The herpes virus has a complex activity as is illustrated by two ailments caused by herpes viruses, namely, cold sores and genital herpes. Oral Herpes Simplex Type 1 affects most Americans by the time they are fifteen years of age. Approximately thirty to fifty percent of the population of the United States is afflicted with subsequent cases of cold sores, generally in the lip area, although not in the mouth. Occasionally the Herpes Simplex 1 virus can migrate along nerve cells invading the central nervous system, primarily the temporal lobe, to cause life-threatening encephalitis.

The patterns of infection, latency and reactivation of genital herpes caused by the Herpes Simplex 2 virus are similar to Type 1 virus. A primary infection, usually resulting from sexual contact with a partner that is shedding virus, causes highly infectious lesions on the genital organs which can spread the virus for about ten days. Immunity against the virus develops, the lesions heal, but yet some of the virus remains in the body, traveling along the nerve cells—this time to the sacral ganglia near the lower spinal cord, where it remains dormant for a time. A recurrent episode of this infection may then be caused by stress or other factors similar to those that trigger cold sores. Recurrence of this virus is more frequent in men and often follows sexual intercourse. Recurrence in women tends to be more severe. It has also been observed that women who have frequent episodes of genital herpes, and thus have high titers of antibodies to Herpes Simplex 2, have a relatively high incidence of cervical cancer.

Two viral infections of the oral mucosa are herpes simplex infections and herpangina.

Herpetic stomatitis represents a primary contact with the herpes simplex virus. After the loss of maternal antibodies to the herpes virus, the child or young adult, as a result of exposure, becomes infected. This commonly results in a condition called herpetic stomatitis. Less common forms of involvement are a herpetic dermatitis, herpetic vulvovaginitis, herpetic conjunctivitis or keratitis, and herpetic meningitis or meningoencephalitis.

Following the development of the primary herpetic disease, an antibody response confers immunity to subsequent manifestations of the primary disease. Recurrent herpetic involvement is usually confined to the lips and its manifestations differ from those of the typical herpetic stomatitis.

Acute herpetic gingivostomatitis usually strikes children and young adults. It has been observed that older people are rarely affected by this condition.

Oral herpetic disease is first manifested by a prodromal period of 24 to 48 hours, after which the oral manifestations appear. Specifically, an acute gingivitis of the marginal and attached gingiva appears and the tongue exhibits vesicular eruption and is coated. The gingivae becomes edematous and reddened. This disease is further characterized by vesicles and ulcers that can form throughout the mouth. The vesicles usually rupture approximately 24 hours after formation, leaving small ulcers surrounded by a zone of erythema. These vesicles can continue to form for up to approximately one week. Within approximately twelve to eighteen days, these lesions tend to disappear, healing without any residual scarring.

Initially, the symptoms may appear similar to other acute infections that exhibit fever, malaise, generalized discomfort and localized pain. Eating becomes difficult due to the gingiva being swollen and the presence of numerous painful ulcers. The temperature in the child ranges from 100° to 104° in the early stages, and returns to normal in approximately five to seven days. In the young adult, systemic manifestations are similar to those found in younger children, but are often less severe, and the temperatures usually remain under 100° F. The lips may be subject to recurrent attacks of grouped vesicular lesions. Herpes Simplex Virus is the etiologic agent. The antibodies against the herpes virus are ineffective at this local site, and recurrent disease can occur despite the presence of antibodies to the disease. It seems that the virus is present in the lip epithelium, and under certain conditions, produces the disease. Some of these conditions are the rays of the sun, trauma, and emotional tension. The lip vesicles are usually size in size and quite numerous in number. They may be localized to a small area of the lips or they may cover the entire mucosa. The duration of herpes labialis is usually seven to ten days, and is often prolonged by a complicating secondary infection of the lesions on the skin close to the muco-cutaneous junction. In recurrent herpes labialis, the mouth is not involved, but there may be labial involvement in primary herpetic stomatitis.

Althouguh recurrent oral herpetic disease is unusual, it can nevertheless occur. These lesions have small vesicles surrounded by erythema. These vesicles rupture rapidly leaving small punctate ulcers. Acute gingivitis, coated tongue, and the sytemic manifestations seen in primary herpetic stomatitis are absent.

DESCRIPTION OF THE INVENTION

It has heretofore been found that potassium nitrate has an amazingly beneficial effect on hypersensitive dentin (U.S. Pat. No. 3,863,006); on canker sores (U.S. Pat. No. 4,191,750); and in the preservation of dental pulp (U.S. Pat. No. 4,343,608). It has now been found through experimental clinical trials that the local symptoms of acute herpetic stomatitis, recurrent oral herpes, recurrent genital and herpes labials are greatly relieved by the topical administration of substances containing potassium nitrate. Specifically, a mouthwash, gel or a cream-type preparation containing potassium nitrate, when applied to these lesions, has been found to be extremely effective and long-lasting in its effect. For reasons not completely understood, the pain elicited by the local lesions is greatly alleviated for hours at a time, and their healing is enhanced, i.e., the time required to heal such lesions is shortened to about one-half its normal time.

It is thought that the potassium nitrate acts on the local lesions by uniquely restoring the normal fluid balance and electrical charges to these tissues, thereby promoting more rapid healing.

In utilizing potassium nitrate for the treatment of herpetic conditions, it is simply necessary to dissolve potassium nitrate crystals in a liquid solution, preferably water, and then the solution so formed is liberally applied to the lesions by rinsing or by means of cotton or other suitable applicators. It has specifically been found that an aqueous solution comprising 5% by weight potassium nitrate works extremely well. On the other hand, an aqueous solution comprising 1% by weight of potassium nitrate is also effective, but not to the extent that a more concentrated solution is. A saturated solution (approximately 20% by weight of the solution) may be used, but the results of a saturated solution are not sufficiently beneficial over that of a 5% solution to justify the expense of including the additional potassium nitrate.

As stated previously, the liberal application of an aqueous solution of potassium nitrate to the herpetic lesions results in a prompt and extremely pronounced elimination of the discomfort and pain. This effect is relatively long lasting, lasting for several hours or more. Initially there may be a stinging sensation to some degree, but this quickly gives way to a feeling of comfort and this is done without producing irritation or discoloring of any of the tissues. It has been noted that this treatment promotes more effective healing, causing the lesions to heal more quickly than untreated lesions, i.e., in approximately one-half the time.

In addition to applying the potassium nitrate to the herpetic lesions in the form of an aqueous solution, it is possible to incorporate potassium nitrate in a non-toxic paste, gel or cream which would then be applied to the herpetic lesions. Furthermore, as previously stated, the liquid solution containing the potassium nitrate could be made merely with water, or it could be included in a mouthwash-type preparation. A paste or cream could be made from any combination of non-toxic vehicles or substances, but it must contain potassium nitrate. For example, a paste was formulated as follows:

| Hydroxyethyl cellulose | 8 grms. |
|---|---|
| Methyl cellulose | 4 grms. |
| KNO$_3$ crystals | 32 grms. |
| Flavoring & coloring, if desired | |

| -continued | |
|---|---|
| H$_2$O | 600 mls. |
| Titanium dioxide | 2 grms. |

The ingredients can be modified to vary the consistency of the paste. By eliminating the titanium dioxide, a gel will result. As with the liquid solution, the amount of KNO$_3$ in the paste or gel may effectively comprise 1% to saturation (approximately 20%) by weight of the composition, although a 5% composition has proven to be highly effective.

An example of a liquid formulation is as follows:

| Mouthwash or glycerol | 66% to 75% |
|---|---|
| Water saturated KNO$_3$ | 34% to 25% |

The liquid, paste, cream or ointment form can be applied as frequently as desired and as deemed necessary with a surprising degree of relief and enhanced healing resulting, without adversely affecting the tissues in any way.

As this invention may be embodied in several forms without departing from the spirit or essential characteristics thereof, the present embodiment is thereofore illustrative and not restrictive, since the scope of the invention is defined by the appended claims rather than by the description preceeding them, and all changes that fall within the metes and bounds of the claims or that form their functional as well as conjointly cooperative equivalents are therefore intended to be embraced by these claims.

What is claimed is:

1. The method of treating herpes simplex lesions so as to relieve discomfort and expedite healing, the method comprising the topical application to said lesions of a composition, the essential ingredient of which is an effective amount of potassium nitrate.

2. The method of claim 1 further characterized in that said composition is a liquid solution.

3. The method of claim 2 further characterized in that said composition is an aqueous solution.

4. The method of claim 3 further characterized in that said potassium nitrate comprises between 1% by weight and saturation of said aqueous solution.

5. The method of claim 3 further characterized in that said potassium nitrate comprises approximately 5% by weight of said aqueous solution.

6. The method of claim 1 further characterized in that said composition is a non-toxic formulation of gel-like consistency.

7. The method of claim 1 further characterized in that said composition is a non-toxic formulation of paste-like consistency.

8. The method of claim 6 further characterized in that said potassium nitrate comprises between 1% and saturation of said gel.

9. The method of claim 7 further characterized in that said potassium nitrate comprises between 1% and saturation of said paste.

* * * * *